(12) United States Patent
Willis et al.

(10) Patent No.: US 7,621,895 B2
(45) Date of Patent: Nov. 24, 2009

(54) NEEDLE ARRAY DEVICES AND METHODS

(75) Inventors: Geoffrey H. Willis, Redwood City, CA (US); Eric Willis, Santa Cruz, CA (US); Shuji Uemura, San Francisco, CA (US); Mike Stewart, San Jose, CA (US); Alfredo Cantu, Pleasanton, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 11/436,709

(22) Filed: May 17, 2006

(65) Prior Publication Data

US 2007/0270757 A1    Nov. 22, 2007

(51) Int. Cl.
*A61M 5/00* (2006.01)

(52) U.S. Cl. .................. 604/173; 604/158; 604/164.01; 604/272

(58) Field of Classification Search ........... 604/164.01, 604/164.02, 164.11, 164.12, 158, 173, 239, 604/264, 272, 523
See application file for complete search history.

(56) References Cited

U.S. PATENT DOCUMENTS

| | | | |
|---|---|---|---|
| 4,578,061 A | 3/1986 | Lemelson | |
| 6,217,554 B1 * | 4/2001 | Green | 604/164.01 |
| 6,554,801 B1 | 4/2003 | Steward et al. | |
| 6,629,949 B1 | 10/2003 | Douglas | |
| 6,689,103 B1 | 2/2004 | Palasis | |
| 6,692,466 B1 * | 2/2004 | Chow et al. | 604/164.01 |
| 6,944,490 B1 | 9/2005 | Chow | |
| 7,087,040 B2 * | 8/2006 | McGuckin et al. | 604/158 |
| 2003/0083645 A1 | 5/2003 | Angel et al. | |
| 2003/0181863 A1 | 9/2003 | Ackley et al. | |
| 2003/0181908 A1 | 9/2003 | Palasis et al. | |
| 2008/0027384 A1 * | 1/2008 | Wang et al. | 604/115 |

FOREIGN PATENT DOCUMENTS

| | | |
|---|---|---|
| DE | 102004063798 | 5/2006 |
| WO | WO 99/48545 | 9/1999 |
| WO | WO 00/67647 | 11/2000 |
| WO | WO 00/74763 | 12/2000 |
| WO | WO 2006/118804 | 11/2006 |

OTHER PUBLICATIONS

Abbott Cardiovascular Systems Inc., PCT Search Report for PCT Application No.PCT/US2007/009790, mailed Oct. 10, 2007 (20 pages).

* cited by examiner

*Primary Examiner*—Kevin C Sirmons
*Assistant Examiner*—Bhisma Mehta
(74) *Attorney, Agent, or Firm*—Blakely, Sokoloff, Taylor & Zafman LLP

(57) ABSTRACT

Methods and delivery devices for maximizing injectate dispersion in lesioned tissue using needle-based injection devices are herein disclosed. The delivery devices include injection devices with various needle arrays and/or modified needle tip configurations. The needle tip configurations can include linear, hooked or corkscrew tips and/or multiple circumferential openings.

6 Claims, 7 Drawing Sheets

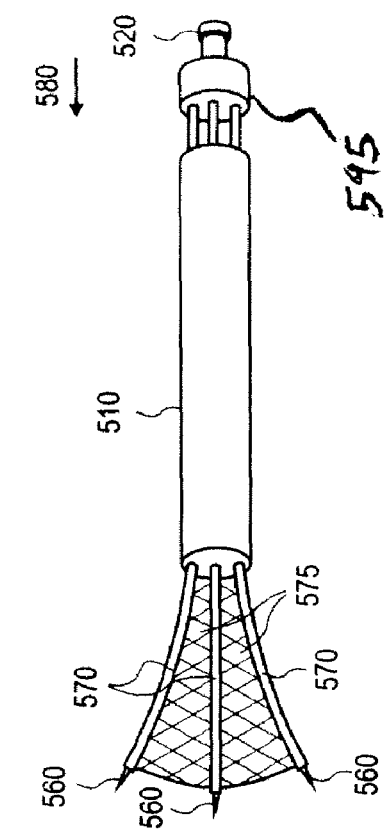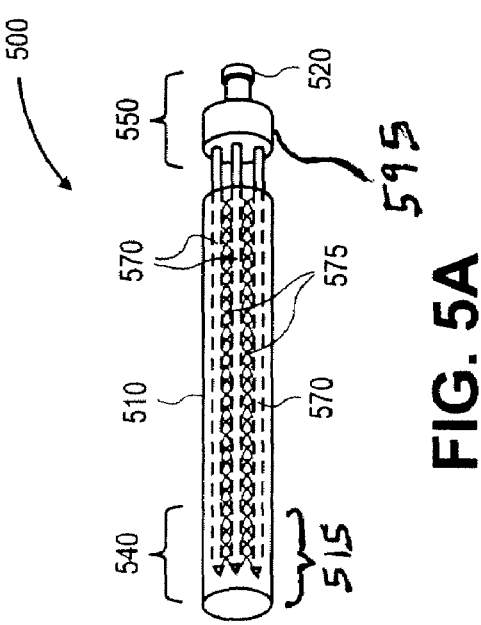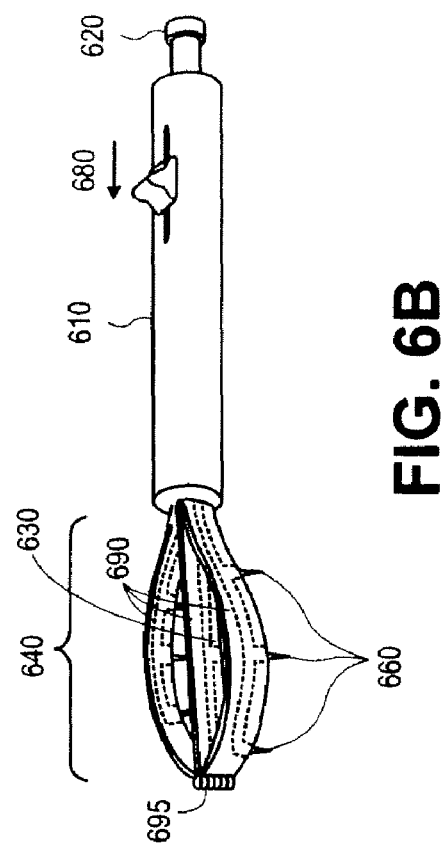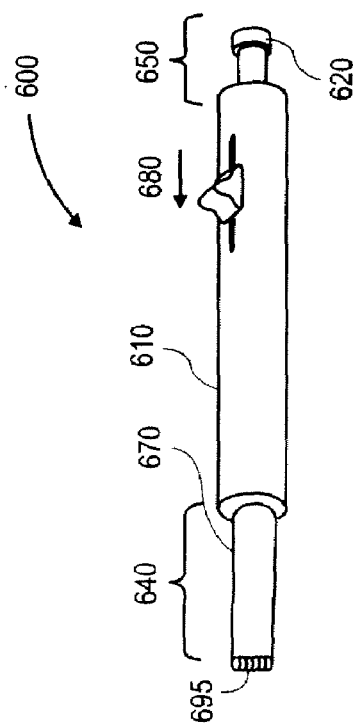

NEEDLE ARRAY DEVICES AND METHODS

FIELD OF INVENTION

Modified needle apparatuses with needle arrays for delivery of substances into or withdrawal from a body.

BACKGROUND OF INVENTION

Percutaneous transluminal coronary angioplasty (PTCA) is a procedure for treating heart disease, particularly, stenosis. "Stenosis" refers to a narrowing or constriction of the diameter of a vessel. In a typical PTCA procedure, a catheter assembly having a balloon portion is introduced percutaneously into the cardiovascular system of a patient via the brachial or femoral artery to treat stenosis at a lesion site. The catheter assembly is advanced through the coronary vasculature until the balloon portion is positioned across the occlusive lesion. Once in position across the lesion, the balloon is inflated to a predetermined size to radially compress the atherosclerotic plaque of the lesion against the inner wall of the artery to dilate the lumen. The balloon is then deflated to a smaller profile to allow the catheter to be withdrawn from the patient's vasculature.

Restenosis of the artery commonly develops over several months after the procedure, which may require another angioplasty procedure or a surgical by-pass operation. "Restenosis" is the reoccurrence of stenosis in a blood vessel or heart valve after it has been treated with apparent success. Restenosis is thought to involve the body's natural healing process. Angioplasty or other vascular procedures often injure the vessel walls, including removing the vascular endothelium, disturbing the tunica intima, and causing the death of medial smooth muscle cells. Excessive neoinitimal tissue formation, characterized by smooth muscle cell migration and proliferation to the intima, follows the injury. Proliferation and migration of smooth muscle cells (SMC) from the media layer to the intima cause an excessive production of extra cellular matrices (ECM), which is believed to be one of the leading contributors to the development of restenosis. The extensive thickening of the tissues narrows the lumen of the blood vessel, constricting or blocking blood flow through the vessel.

To reduce the chance of the development of restenosis, treatment substances can be administered to the treatment site. For example, anticoagulant and antiplatelet agents are commonly used to inhibit the development of restenosis. In order to provide an efficacious concentration to the target site, systemic administration of such medication often produces adverse or toxic side effects for the patient. Local delivery is a preferred method of treatment in that smaller total levels of medication are administered in comparison to systemic dosages, but are concentrated at a specific site. Local delivery, thus, produces fewer side effects and achieves more effective results.

Techniques for the local delivery of a treatment substance into the tissue surrounding a vessel are disclosed in U.S. Pat. Nos. 6,944,490, 6,692,466 and 6,554,801 to Chow et al. In some applications, such techniques include a catheter with a needle cannula slidably disposed in a needle lumen and a balloon, which is coupled to the distal end of the catheter. When the balloon is inflated the needle lumen is brought into close engagement with the tissue and the needle cannula can be moved between a position inboard of the catheter distal surface and a position where the needle cannula is projected outboard of the catheter to deliver the treatment substance to the tissue.

Needles which are used in conjunction with percutaneous injection devices and open-chest surgical injection devices generally include beveled single-port needle tips. Some of the problems associated with these types of needle tips include backflow of the injectate to non-focal areas, damage to surrounding tissue due to high focal injection pressure and reduced treatment agent dispersion due to localized delivery from a single port. Some studies have shown that up to 90 percent of the injectate never reaches the target tissue area due to backflow. As a result, treatment using needles often requires multiple injections which can result in increased pain and risk to the patient in addition to increased tissue damage due to multiple puncture wounds.

The treatment of organs with injection devices, in particular dynamic organs, also presents unique challenges. For example, the heart will generally be contracting during a treatment which increases backflow during each muscle contraction and decreases treatment agent dispersion. Moreover, injection devices with a single needle can be inadequate to treat a large injury region on the heart.

SUMMARY OF INVENTION

Methods and delivery devices for maximizing injectate dispersion in lesioned tissue using needle-based injection devices are herein disclosed. The delivery devices include injection devices with various needle arrays and/or modified needle tip configurations. The needle tip configurations can include, but are not intended to be limited to, linear, hooked, helical or corkscrew tips and/or one or more multiple circumferential openings. The needle tip configurations can additionally include recesses, grooves and/or indentations.

BRIEF DESCRIPTION OF DRAWINGS

FIGS. 5A-5B illustrate a second alternative embodiment of a modified needle apparatus with a needle array.

FIGS. 6A-6B illustrate a third embodiment of a modified needle apparatus with a needle array.

DETAILED DESCRIPTION

Delivery Devices

Figure 1A:
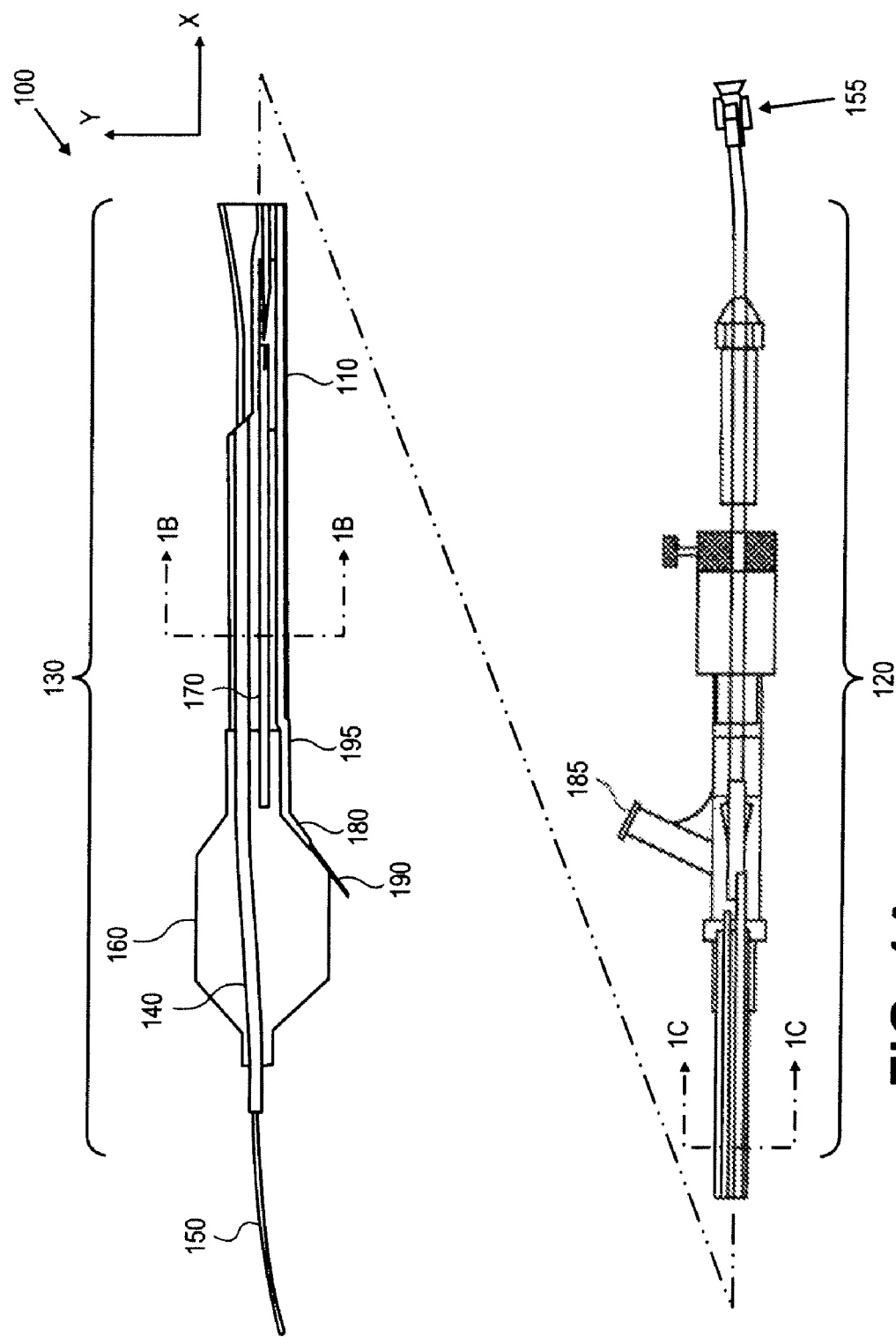
FIGS. 1A-1C illustrate a substance delivery assembly which may be used in conjunction with embodiments of the present invention.
Figure 1B:
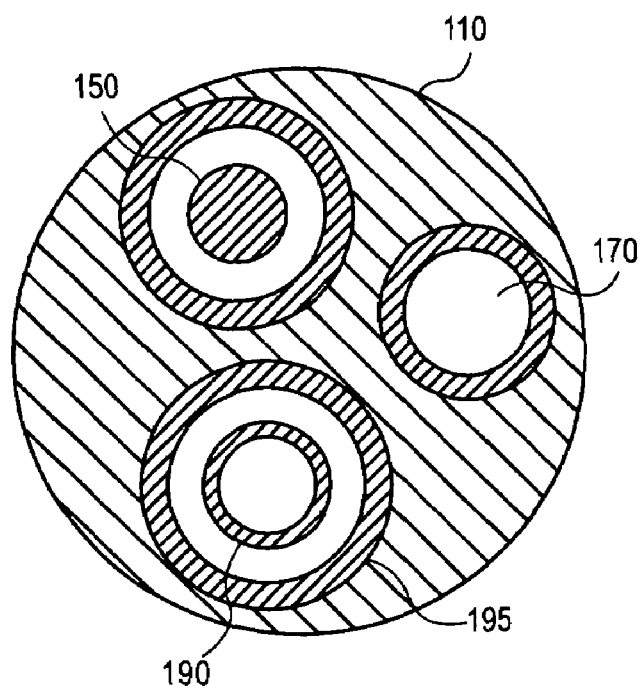
Figure 1C:
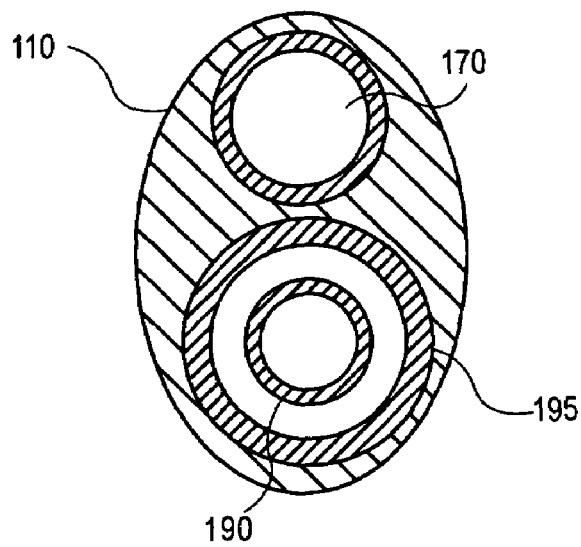

FIGS. 1A, 1B, and 1C illustrate a delivery assembly or device which can be used in conjunction with embodiments of the present invention. In general, the delivery assembly provides a system for delivering a substance, such as a treatment agent or a combination of treatment agent, to or through a desired area of a vessel in order to treat a localized area of the vessel or to treat a localized area of tissue located adjacent to the vessel. The delivery assembly includes a catheter assembly 100, which is intended to broadly include any medical device designed for insertion into a vessel to permit injection and/or withdrawal of fluids, to maintain the patency of the vessel, or for any other purpose. It is contemplated that the delivery assembly has applicability for use with any vessel or organ, including blood vessels, urinary tract, intestinal tract, kidney ducts, wind pipes, and the like.

In one embodiment, catheter assembly 100 is defined by an elongated catheter body 110 having a proximal end 120 and a distal end 130. Catheter assembly 100 can include a guidewire lumen 140 for allowing catheter assembly 100 to be fed and maneuvered over a guidewire 150. A balloon 160 is incorporated at distal end 130 of catheter assembly 100 and is in fluid communication with an inflation lumen 170 of catheter assembly 100.

Balloon 160 may be inflated by the introduction of a liquid into inflation lumen 170. Liquids containing treatment and/or diagnostic agents may also be used to inflate balloon 160. In one embodiment, balloon 160 may be made of a material that is permeable to such treatment and/or diagnostic liquids. To inflate balloon 160, the fluid can be supplied into inflation lumen 170 at a predetermined pressure, for example, between about 1 and 20 atmospheres. The specific pressure depends on various factors, such as the thickness of balloon wall, the material from which balloon wall is made, the type of substance employed, and the flow-rate that is desired.

Catheter assembly 100 also includes a substance delivery assembly 180 for injecting a substance into a wall of a vessel or tissue located adjacent to the vessel. In one embodiment, delivery assembly 180 includes a needle 190 movably disposed within a hollow delivery lumen 195. Needle 190 includes a lumen with an inside diameter of, representatively, about 0.08 inches (0.20 centimeters). Delivery lumen 195 extends between distal end 130 and proximal end 120. Delivery lumen 195 can be made from any suitable material, such as polymers and copolymers of polyamides, polyolefins, polyurethanes and the like. Access to the proximal end of delivery lumen 195 for insertion of needle 190 is provided through a hub 185.

Needle 190 is slidably or movably disposed in delivery lumen 195. Needle 190 includes a tissue-piercing tip having a dispensing port (not shown). The dispensing port is in fluid communication with a central lumen (not shown) of needle 190. In one embodiment, the central lumen of needle 190 can be pre-filled with a measured amount of a substance. The central lumen of needle 190 connects the dispensing port with substance injection port 155, which is configured to be coupled to various substance dispensing means of the sort well known in the art, for example, a syringe or fluid pump. Injection port 155 allows a measured substance to be dispensed from a dispensing port as desired or on command. In some applications, catheter assembly 100 enters percutaneously through an arterial vessel of the heart.

Figure 2A:
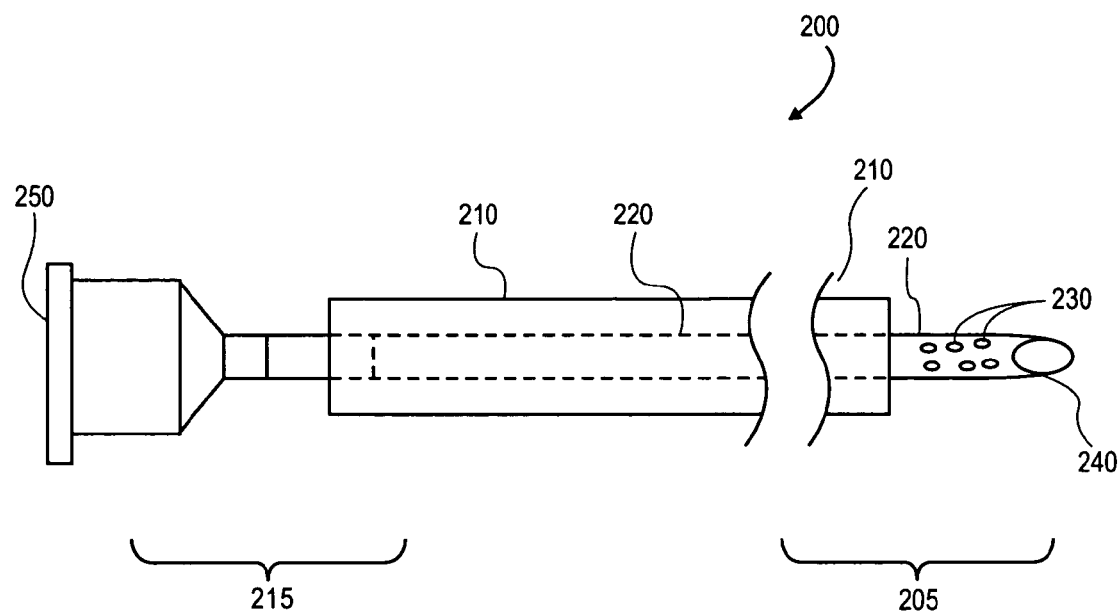
FIG. 2A illustrates an alternative delivery assembly which may be used in conjunction with embodiments of the present invention.

FIG. 2A illustrates a cross-sectional side view of an alternative delivery device or apparatus which can be used in conjunction with embodiments of the present invention. In general, delivery assembly 200 provides an apparatus for delivering a substance, such as a treatment agent, to or through a desired area of a blood vessel (a physiological lumen) or tissue in order to treat a localized area of the blood vessel or to treat a localized area of tissue located adjacent to the blood vessel.

Referring to FIG. 2A, delivery assembly 200, in one embodiment, may be in the form of a catheter device that includes delivery lumen 210 that may be formed in a larger catheter body (not shown). The larger catheter body may include one or more lumens to accommodate, for example, a guidewire, an inflation balloon, and/or an imaging device. Further, such a catheter body may accommodate one or more delivery lumens, such as delivery lumen 210. Delivery lumen 210, in this example, extends between distal portion 205 and proximal portion 215 of delivery assembly 200. Delivery lumen 210 can be made from any suitable material, such as polymers and co-polymers of polyamides, polyolefins, polyurethanes, and the like.

In one embodiment, delivery assembly 200 includes needle 220 movably disposed within delivery lumen 210. Needle 220 is, for example, a stainless steel hypotube that extends a length of the delivery assembly. Needle 220 includes a lumen with an inside diameter of, representatively, about 0.16 inches (0.40 centimeters). In one example for a retractable needle catheter, needle 220 has a length of about 40 inches (1.6 meters) from distal portion 205 to proximal portion 215. The needle 220 may include at least one opening 230. At an end of proximal portion 215 is adapter 250 of, for example, a female luer housing.

When loaded, a substance may be introduced according to known substance delivery techniques such as by advancing tip 240 of needle 220 into tissue (e.g., a wall of a blood vessel) and delivering the substance through back pressure (e.g., pressure applied at proximal portion 215, such as by a needle luer). In some applications, delivery assembly 200 enters percutaneously through the left ventricle of the heart.

Figure 2B:
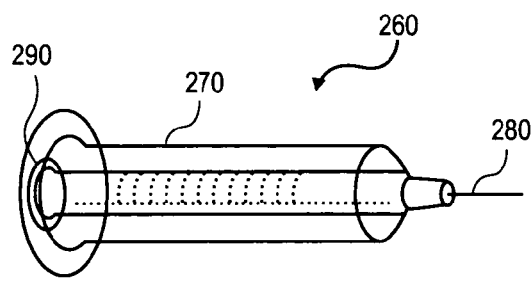
FIG. 2B illustrates a second alternative delivery assembly which may be used in conjunction with embodiments of the present invention.

FIG. 2B illustrates an alternative delivery assembly which can be used in conjunction with embodiments of the present invention. In some embodiments, delivery device 260 is a syringe. Delivery device 260 may include a body 270, a needle 280 and a plunger 290. A shaft of plunger 290 has an exterior diameter slightly less than an interior diameter of body 270 so that plunger 290 can, in one position, retain a substance in body 270 and, in another position, push a substance through needle 280. Syringes are known by those skilled in the art. In some applications, delivery device 260 may be applied directly to a treatment site during an open-chest surgery procedure.

Needle Arrays

In some embodiments, modified needle apparatuses can be used to maximize injectate dispersion into tissue or organs. In some embodiments, the modified needle apparatuses can have an array of needles configured in various conformations to maximize injectate dispersion. In some embodiments, methods, apparatuses or compositions can be used to control dynamic organs to isolate a target tissue region thereby maximizing injectate dispersion.

Figure 3A:
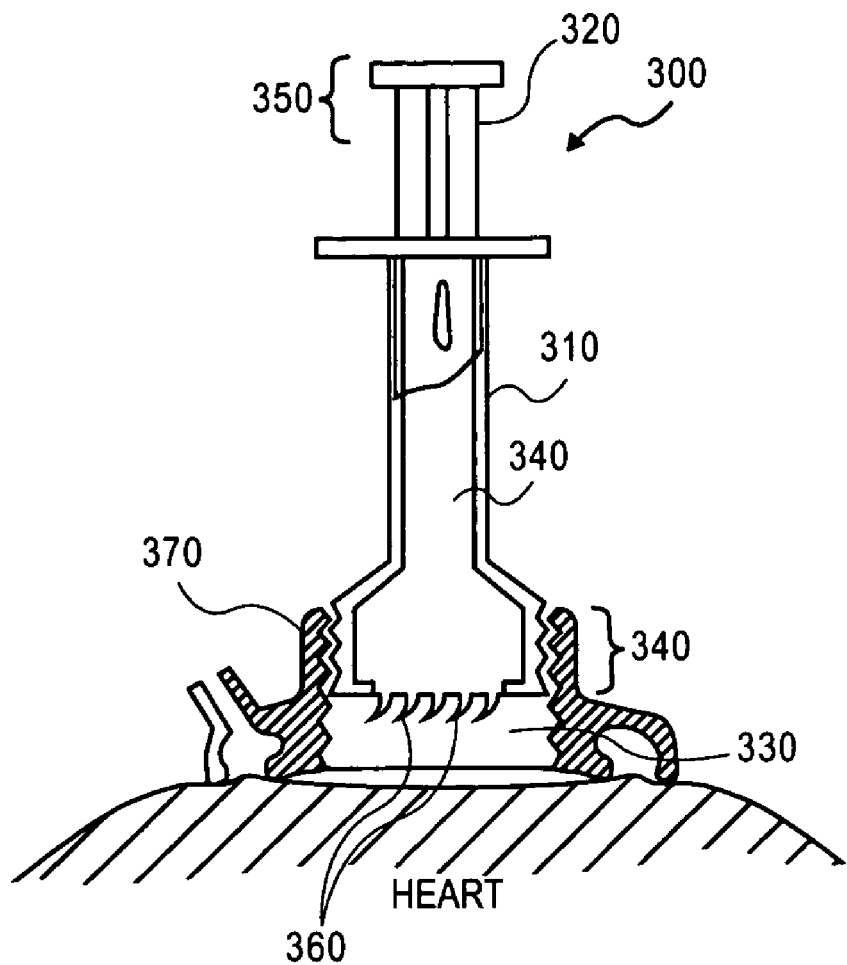
FIGS. 3A-3B illustrate an embodiment of a modified needle apparatus with a needle array.
Figure 3B:
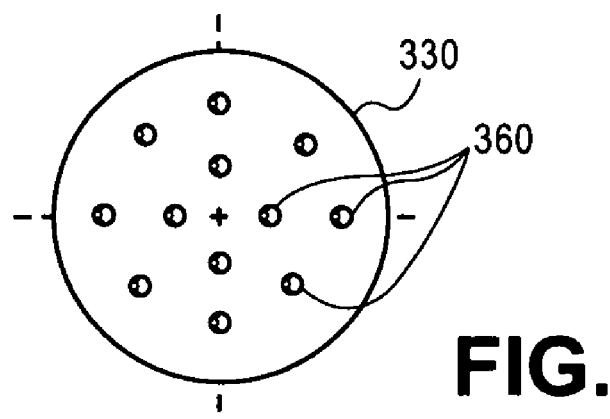

FIGS. 3A-3B illustrate an embodiment of a modified needle apparatus. A needle apparatus 300 includes a body 310, a plunger 320 (located at proximal end 350 of body 310) and an injectate region 330 (located at distal end 340). Injectate region 330 can include a series of needles 360 with openings (not shown) arranged in a suitable pattern to maximize injectate dispersion. Needles 360 can be in fluid communication with a fluid reservoir 340 to deliver injectate. Needles 360 can each have a diameter in the range of about 0.005 to 0.05 inches and a penetrating length in the range of about 0.5 to about 5.0 millimeters. In one embodiment, needles 360 can be arranged in a circular pattern, as shown in FIG. 3B (front view of injectate region 330). In some embodiments, needles 360 can be shaped in specific configurations, such as corkscrews or hooks. Such configurations can maximize injectate dispersion by providing multiple entries for injectate at a treatment site and by creating a non-linear pathway for the injectate to disperse throughout a wider area thereby decreasing backflow. As would be understood by one skilled in the art, other configurations can be provided in accordance with the teachings herein.

To assist in targeted delivery of the injectate, needle apparatus 300 can include an anchor 370 disposed adjacent to distal end 340. The anchor 370 includes a vacuum opening in fluid communication with a vacuum source (not shown) and helps to stabilize a treatment site when needle apparatus 300 is positioned thereon. For example, when the area to be treated is on the heart, the anchor 370 may be necessary to specifically target the treatment site because the heart will be continually contracting throughout an application of injectate. Apparatuses which stabilize the heart during such procedures include the XPOSE.™ 3 Access Device and the XPOSE.™ 4 Access Device developed by Advanced Cardiovascular Systems, Inc., Santa Clara, Calif. The embodiments shown in FIGS. 3A-3B illustrate a needle apparatus to be used in an open-chest procedure, however, it is also contemplated that a modified version can be used with a catheter assembly.

Figure 4A:
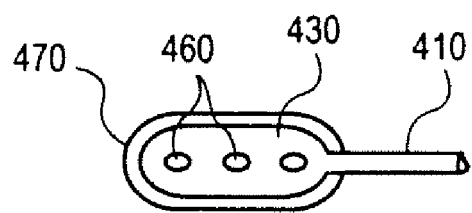
FIGS. 4A-4B illustrate an alternative embodiment of a modified needle apparatus with a needle array.
Figure 4B:
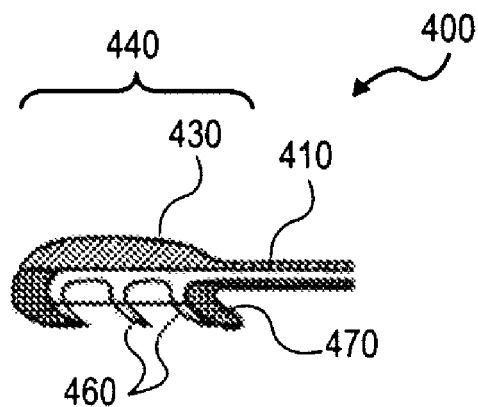
Figure 4C:
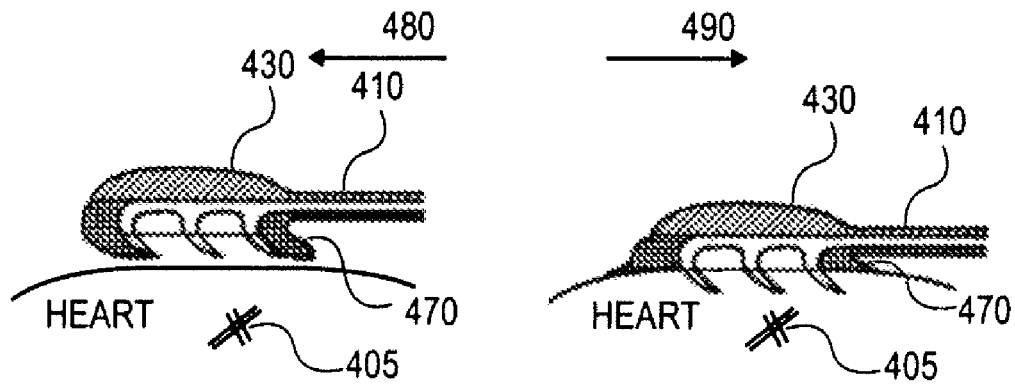
FIG. 4C shows the embodiment of a needle apparatus with a needle array positioned over a treatment site and then penetrating a treatment site.

FIGS. 4A-4C illustrate an alternative embodiment of a modified needle apparatus which may be used for percutaneous injection using a catheter assembly. A modified needle apparatus 400 includes a body 410 with an injectate region 430 covered by a moveable rubber skirt 470 located at a distal end 440. Injectate region 430 can include a series of needles 460 with openings (not shown) arranged in a suitable pattern. The needles 460 can be in fluid communication with a fluid reservoir to deliver injectate. Additionally, needles 460 may be linear or directional. In one embodiment, needles 460 may be arranged in a linear fashion (see FIG. 4B) and angled in a direction away from the pathway in which needle apparatus 400 is delivered to the treatment site.

In one application in which the area to be treated is on heart 405, representatively shown in FIG. 4C, needle apparatus 400 may be inserted intravenously (arrow 480) through a blood vessel until it reaches the treatment site. After insertion and throughout the positioning of needle apparatus 400, rubber skirt 470 serves to protect the needles 460 from puncturing healthy tissue as it is being delivered to the treatment site. Moreover, in this embodiment, needles 460 are angled in a direction away from the pathway in which the needle apparatus 400 is delivered to the treatment site thereby reducing inadvertent puncturing of healthy tissue during delivery. To release injectate, needle apparatus 400 may be positioned at a point slightly past the treatment site. Needle apparatus 400 may then be retracted (arrow 490) such that needles 460 hook into the treatment site. The moveable rubber skirt 470 may splay adjacent to the injectate region 430 to stabilize and localize the injectate as it is dispensed through needles 460 from a fluid reservoir (not shown). In this manner, injectate dispersion can be maximized through multiple entries and by creating a non-linear pathway for the injectate to disperse throughout a wider area thereby decreasing backflow.

FIGS. 5A-5B illustrate another embodiment of a modified needle apparatus. A modified needle apparatus 500 includes a body 510 with a distal end 515 and a proximal end 550. An extension and retraction knob 520 can be located at proximal end 550. In some embodiments, the body can be approximately tubular and can house at least one retractable tube 570. Retractable tubes 570 may be deployable by a spring-loaded mechanism or any other suitable mechanism. A needle 560 can be located at the distal end of each retractable tube 570. Needle 560 can be in fluid communication with lumen 595 to provide fluid communication with a fluid reservoir to deliver injectate.

In one application, needle apparatus 500 may be directed to a treatment site. The needle apparatus 500 remains in a retracted state with distal end 540 of tube 570 positioned in body 510 (FIG. 5A) with the series of retractable tubes 570 resting in body 510 until the injectate is ready to be delivered to the treatment site. Once positioned on the treatment site, knob 520 may be depressed (arrow 580) so that the retractable tubes 570 can extend from body 510 into an exposed position (e.g. as shown in FIG. 5B) or into the treatment site (FIG. 5B). In some embodiments, retractable tubes 570 flare outwardly in a non-linear pathway to contact multiple areas on the treatment site thereby maximizing injectate dispersion. In some embodiments, retractable tubes 570 may be connected by flexible webbing 575 to stabilize the deployment of retractable tubes 570. Thus, the injection pattern may be controllable and repeatable.

FIGS. 6A-6B illustrate still another embodiment of a modified needle apparatus. A modified needle apparatus 600 includes a body 610 with a distal end 640 and a proximal end 650. An extension and retraction knob 620 can be located at proximal end 650, while a hollow flexible member 670 may be located at distal end 640. A needle array 630 may be located within flexible member 670. Needle array 630 can include at least one needle 660. Each needle 660 can be in fluid communication with a fluid reservoir to deliver injectate.

In one application, needle apparatus 600 may be directed to a treatment site. Needle apparatus 600 remains in a retracted state (FIG. 6A) with the needle array 630 in a retracted position until the injectate is ready to be delivered to the treatment site. Once positioned on the treatment site, the knob 620 may be engaged (arrow 680) so that the needle array 630 extends from the flexible member 670 and into the treatment site (FIG. 6B). Simultaneously, the flexible member may splay outwardly into at least two arms 690. The arms 690 may be connected by a hinge 695. In this manner, the injection pattern may be controllable and repeatable.

Figure 7:
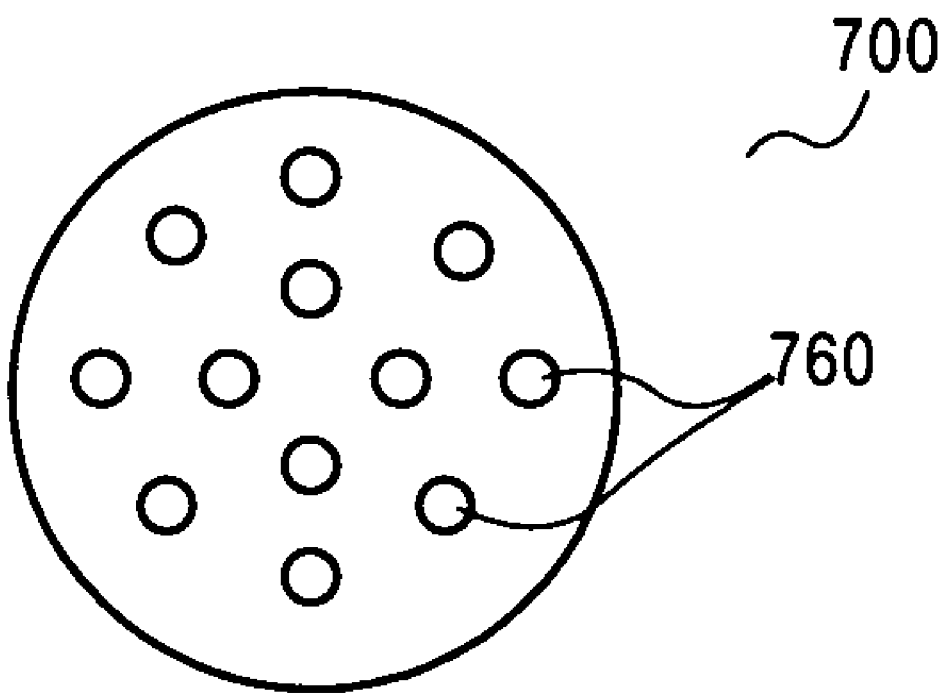
FIG. 7 illustrates an embodiment of a positioning device which may be used pursuant to methods of the present invention.

FIG. 7 illustrates a device which can be used to isolate a target tissue region to maximize injectate dispersion. The device may be, for example, a plastic plate 700 with an array of openings 760 attached to a distal end of a vacuum source (not shown). Plate 700 may be any suitable configuration. In some applications, plate 700 may be positioned over a treatment site during an open-chest procedure. The vacuum source may be used to immobilize the treatment site in preparation for delivering an injectate. Plate 700 can be made of an elastomer, such as silicon or any other biocompatible material, and can serve as an isolating mechanism for delivery of injectate to, for example, a treatment site on the heart. In one application, plate 700 is positioned over the treatment site by a positioning device (not shown). Plate 700 thereby serves to isolate the target tissue region. A needle assembly or a syringe, such as those described in relation to FIGS. 1A-1B, may then be used to deliver injectate.

In any of the above-described embodiments, the needles may include one or more circumferential openings to maximize injectate dispersion. In some embodiments, a substance may be added to the injectate to temporarily reduce contractility of the heart in order to maximize injectate dispersion throughout the treatment site. Such substances include, but are not limited to, heparin, diltiazem and verapamil.

From the foregoing detailed description, it will be evident that there are a number of changes, adaptations and modifications of the present invention which come within the province of those skilled in the part. The scope of the invention includes any combination of the elements from the different species and embodiments disclosed herein, as well as subassemblies, assemblies and methods thereof. However, it is intended that all such variations not departing from the spirit of the invention be considered as within the scope thereof.

What is claimed is:

1. A substance delivery device comprising:
   a body comprising a proximal end, a distal end and having a lumen;
   a retractable needle array at the distal end comprising a plurality of retractable tubes coupled between a plurality of needles and the lumen, the plurality of needles in fluid communication with the plurality of retractable tubes and with the lumen;
   flexible webbing connected to the plurality of retractable tubes and between the plurality of retractable tubes to stabilize a deployment of the needles; and
   a knob at the proximal end connected to the needle array within the body, wherein the knob moves the needle array from a retracted position to an exposed position to cause the deployment of the needles,
   wherein, in an exposed position, each of the plurality of needles defined a non-linear pathway for an injectate to be dispersed therethrough.

2. The device of claim 1, wherein each of the plurality of needles comprises multiple circumferential openings.

3. The device of claim 1, wherein each of the plurality of needles comprises a hook configuration.

4. The device of claim 1, wherein each of the plurality of needles comprises a corkscrew configuration.

5. The device of claim 1, wherein the needle array flares out to form a circular pattern in the exposed position.

6. The device of claim 1, wherein the webbing stabilizes the deployment of the plurality of retractable tubes and causes an injection pattern of the needle array to be controllable and repeatable.

* * * * *